(12) United States Patent
Haziza

(10) Patent No.: US 11,376,084 B2
(45) Date of Patent: Jul. 5, 2022

(54) SURGICAL TOOL COUPLER TO ROBOTIC SYSTEM

(71) Applicant: Premia Spine Ltd., Ramat Poleg (IL)

(72) Inventor: Rafi Haziza, Kiryat Bialik (IL)

(73) Assignee: Premia Spine Ltd., Ramat Poleg (IL)

( * ) Notice: Subject to any disclaimer, the term of this patent is extended or adjusted under 35 U.S.C. 154(b) by 180 days.

(21) Appl. No.: 16/486,158

(22) PCT Filed: Feb. 18, 2018

(86) PCT No.: PCT/IB2018/050986
§ 371 (c)(1),
(2) Date: Aug. 15, 2019

(87) PCT Pub. No.: WO2018/154420
PCT Pub. Date: Aug. 30, 2018

(65) Prior Publication Data
US 2020/0054402 A1 Feb. 20, 2020

Related U.S. Application Data

(60) Provisional application No. 62/462,425, filed on Feb. 23, 2017.

(51) Int. Cl.
*A61B 34/30* (2016.01)
*A61B 17/00* (2006.01)
*A61B 17/58* (2006.01)

(52) U.S. Cl.
CPC ........ *A61B 34/30* (2016.02); *A61B 17/00234* (2013.01); *A61B 17/58* (2013.01); *A61B 2017/00477* (2013.01)

(58) Field of Classification Search
CPC . A61B 19/201; A61B 19/203; A61B 19/5244; A61B 17/00; A61B 17/58; A61B 17/00234; A61B 34/30; A61B 2017/00477
See application file for complete search history.

(56) References Cited

U.S. PATENT DOCUMENTS

2014/0350346 A1* 11/2014 Oberlander ............ A61B 90/57
600/204
2016/0128547 A1* 5/2016 Ogawa ............... A61B 1/00055
600/107

FOREIGN PATENT DOCUMENTS

WO 2016/166662 10/2016

OTHER PUBLICATIONS

PCT Search Report PCT/IB2018/050986, dated Jun. 20, 2018.

* cited by examiner

*Primary Examiner* — Vi X Nguyen
(74) *Attorney, Agent, or Firm* — Dekel Patent Ltd.; David Klein

(57) ABSTRACT

A surgical tool coupler (10) includes a housing (12) with a door (14). The door (14) and housing (12) include mating structures (18, 20) that mate with each other when the door (14) is closed. The housing (12) includes a robotic interface (26) which is connectable to a portion of a robotic surgery system (28).

4 Claims, 1 Drawing Sheet

SURGICAL TOOL COUPLER TO ROBOTIC SYSTEM

FIELD OF THE INVENTION

The present invention relates generally to methods and apparatus for minimally invasive surgery on spinal structures, and particularly to a coupler to couple a surgical tool to a robotic system for surgery, such as spinal surgery.

BACKGROUND OF THE INVENTION

In robotically-assisted or telerobotic surgery, a surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each performs various functions for the surgeon, e.g., holding or driving a needle, grasping a blood vessel, or dissecting, cauterizing or coagulating tissue.

PCT Patent Application WO 2016/166662 describes a spinal tool for affixing pedicle screws to vertebral pedicles and mounting rods to the pedicle screws, such as for fusion or dynamic stabilization. In one example, the device enables inserting a K-wire through a lumen of a cannulated surgical tool. If, for example, the tool is a screwdriver, the K-wire also passes through the lumen of the screw. The device is easily used to position the K-wire so it protrudes a little bit (e.g., a few mm) beyond the distal tip of the screw or surgical tool. The device is then used to lock the K-wire with respect to the screw or tool. The device is adjustable so that its proximal end is flush with the proximal end of the K-wire, so that the surgeon can hammer or otherwise apply force on the proximal end of the device in order to advance the K-wire and screw or tool together. The K-wire breaches the cortical bone (or other spinal structure which the surgeon wishes to breach) and brings the tip of the cannulated screw or tool to the bone surface. From there, the surgeon can screw in the pedicle screw or advance the tool without concern for slipping. Without the device, the screw or tool can slip at the point of entry.

It would be desirable to be able to couple the spinal tool to a robotic system, so the surgical tool can be easily used with the robotic system and easily dismantled therefrom.

SUMMARY OF THE INVENTION

The present invention seeks to provide a coupler to couple a surgical tool to a robotic system for surgery, as described in more detail further below.

The coupler of the present invention may be used to couple the spinal surgical tool, such as but not limited to, the tool of WO 2016/166662, to a portion of a robotic system, such as but not limited to, the robotic arm of the system.

There is thus provided in accordance with an embodiment of the present invention a surgical tool coupler including a housing with a door, the door and the housing including mating structures that mate with each other when the door is closed; and wherein the housing includes a robotic interface which is connectable to a portion of a robotic surgery system.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figures 1A, 1B:
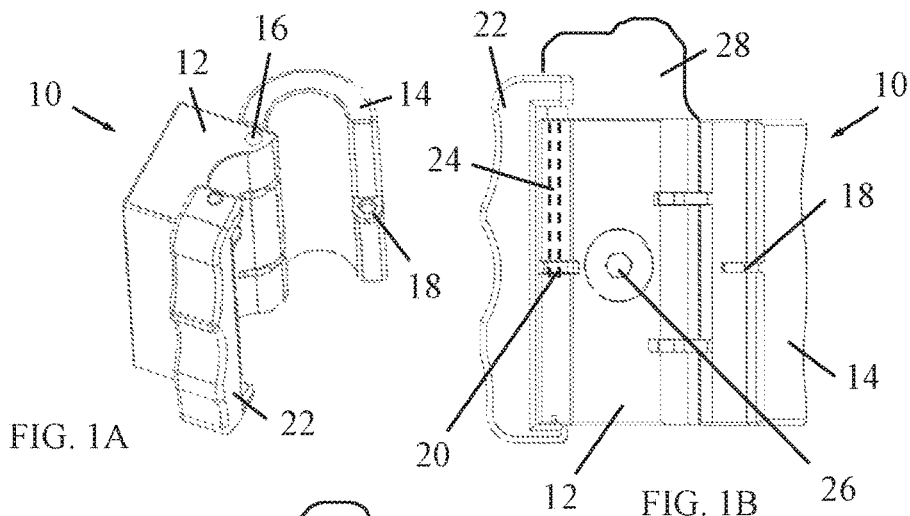
FIGS. 1A, 1B and 1C are simplified perspective, front-view and perspective illustrations of a surgical tool coupler, constructed and operative in accordance with a non-limiting embodiment of the present invention, FIGS. 1A and 1B showing the coupler in an open position and FIG. 1C showing the coupler in a closed position.
Figure 1C:
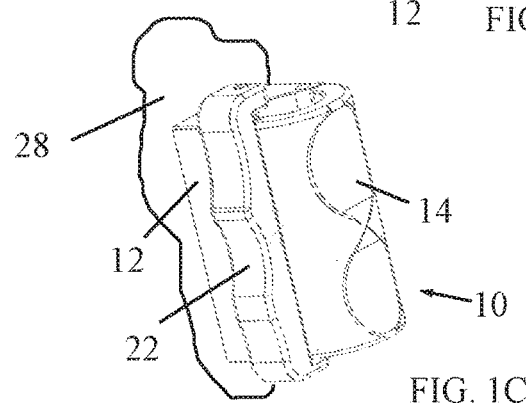

Reference is now made to FIGS. 1A-1C, which illustrate a surgical tool coupler 10, constructed and operative in accordance with a non-limiting embodiment of the present invention.

Surgical tool coupler 10 includes a housing 12 with a door 14, which may be hinged to housing 12 by a hinge 16. Door 14 and housing 12 may include mating structures that mate with each other when the door 14 is closed. For example, door 14 may include a lug 18 (FIG. 1A) that mates with a recess 20 (FIG. 1B) formed in housing 12. Door 14 may be secured to housing 12 in the closed position (shown in FIG. 1C) such as by a closure element 22, which may include a bolt 24 that passes through an aperture in lug 18 and through recess 20. Alternatively, the mating structures of door 14 and housing 12, which mate with each other when the door 14 is closed, may be fasteners that snap or click together when the door is closed.

Housing 12 includes a robotic interface 26 which is connectable to a portion of a robotic surgery system 28, such as a robotic arm of a robotically-assisted or telerobotic surgery system. In the illustrated embodiment, robotic interface 26 includes a mounting screw that passes through housing 12 into the portion of the robotic system 28.

Figures 2A, 2B, 2C:
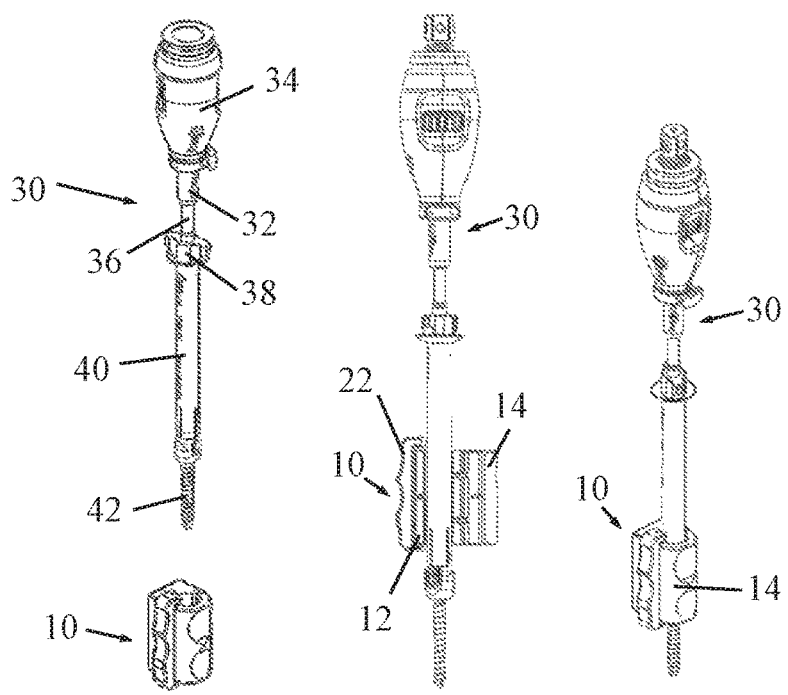
FIGS. 2A-2C are simplified pictorial illustrations of a surgical tool, respectively before, during and after insertion in the tool coupler of FIGS. 1A-1C.

Reference is now made to FIGS. 2A-2C, which illustrate a surgical tool 30, respectively before, during and after insertion in the tool coupler 10.

Surgical tool 30 may be similar to the tool of WO 2016/166662, but the invention is not limited to this tool. Surgical tool 30 may include a distal interface member 32 and a handle 34. Distal interface member 32 includes a connecting element 36 for connecting to a surgical implement 38, such as a screwdriver that can pass through a tower 40 for screwing a pedicle screw 42. Alternatively, the surgical implement 38 may include, without limitation, a screw, a tap, a bore, an awl, a probe, or a jamshidi needle and the like.

Robotic interface 26 may first be secured to the portion (e.g., robotic arm) of the robotic system 28, such as by tightening the mounting screw of robotic interface 26. Surgical tool 30 may be secured to tool coupler 10 by placing the tool in housing 12, and then securely closing the door 14. In other embodiments, the surgical tool 30 may be first secured to the coupler 10 and afterwards the coupler 10 may be secured to the robotic system 28.

What is claimed is:

1. Apparatus comprising:
   a surgical tool coupler comprising a housing with a door, said door and said housing comprising mating structures that mate with each other when said door is closed; and
   wherein said housing comprises a robotic interface which is connectable to a portion of a robotic surgery system, and
   a closure element configured to secure said door to said housing when said door is closed, wherein said closure element has a first portion parallel to a longitudinal axis of said housing, the longitudinal axis extending between first and second end faces of said housing, and said closure element has a second portion that extends transverse to said first portion over said first end face and a third portion that extends transverse to said first portion over said second end face; and wherein said first portion of said closure element is formed with outer concave indentations.

2. The apparatus according to claim 1, wherein said mating structures comprise a lug on said door that mates with a recess in said housing.

3. The apparatus according to claim 1, wherein said closure element comprises a bolt that passes through a lug on said door and a recess in said housing.

4. The apparatus according to claim 1, wherein said door is hinged to said housing by a hinge.

\* \* \* \* \*